(12) United States Patent
Juretich et al.

(10) Patent No.: US 9,821,151 B2
(45) Date of Patent: Nov. 21, 2017

(54) INFUSION PUMP CASSETTE HAVING FINGER-BYPASSED IN-LINE OCCLUDER

(71) Applicant: Zevex, Inc., Salt Lake City, UT (US)

(72) Inventors: Jeffery T. Juretich, Herriman, UT (US); Michael A. Marshall, Herriman, UT (US)

(73) Assignee: Zevex, Inc., Salt Lake City, UT (US)

( * ) Notice: Subject to any disclaimer, the term of this patent is extended or adjusted under 35 U.S.C. 154(b) by 0 days.

(21) Appl. No.: 15/026,455

(22) PCT Filed: Jul. 17, 2015

(86) PCT No.: PCT/US2015/040860
§ 371 (c)(1),
(2) Date: Mar. 31, 2016

(87) PCT Pub. No.: WO2016/099604
PCT Pub. Date: Jun. 23, 2016

(65) Prior Publication Data
US 2016/0339225 A1 Nov. 24, 2016

Related U.S. Application Data

(60) Provisional application No. 62/093,198, filed on Dec. 17, 2014.

(51) Int. Cl.
*A61M 39/12* (2006.01)
*A61M 5/142* (2006.01)
(Continued)

(52) U.S. Cl.
CPC ............ *A61M 39/12* (2013.01); *A61M 5/142* (2013.01); *A61M 5/162* (2013.01); *A61M 39/28* (2013.01);
(Continued)

(58) Field of Classification Search
CPC ...... A61M 39/10; A61M 39/22; A61M 29/38; A61M 39/288; A61M 39/12; A61M 5/142; A61M 2205/12
See application file for complete search history.

(56) References Cited

U.S. PATENT DOCUMENTS 7,815,612 B2   10/2010   Cise et al.
9,464,741 B2 *  10/2016  Lewis ................ F16L 37/0841
(Continued)

FOREIGN PATENT DOCUMENTS

JP            S6110704         1/1986

*Primary Examiner* — Nathan R Price
*Assistant Examiner* — Melissa A Snyder
(74) *Attorney, Agent, or Firm* — Hodgson Russ LLP

(57) ABSTRACT

A cassette for operatively connecting administration set tubing to an infusion pump includes a thumb tab having a thumb surface, and a tubing connector having an in-line occluder spaced laterally from the thumb tab. The cassette is configured such that a user's hand will cradle the cassette by pressing a thumb of the user's hand against the thumb surface and wrapping at least one finger of the user's hand around and under the thumb tab, whereby a user may apply pressure to tubing connected to the tubing connector at a location corresponding to the in-line occluder in a direction generally opposite to a direction in which the thumb is pressed against the thumb surface, thereby bypassing the in-line occluder and allowing flow through the tubing.

5 Claims, 4 Drawing Sheets

(51) Int. Cl.
  *A61M 5/162* (2006.01)
  *A61M 39/28* (2006.01)
  *A61M 5/14* (2006.01)

(52) U.S. Cl.
  CPC ... *A61M 39/284* (2013.01); *A61M 2005/1402* (2013.01); *A61M 2205/12* (2013.01)

(56) References Cited

U.S. PATENT DOCUMENTS

| | | | |
|---|---|---|---|
| 2009/0112064 A1* | 4/2009 | Levey | A61B 1/00135 600/114 |
| 2009/0312719 A1* | 12/2009 | Chew | A61M 5/16881 604/251 |
| 2010/0057058 A1* | 3/2010 | Ziegler | A61M 5/16886 604/890.1 |
| 2010/0280430 A1* | 11/2010 | Caleffi | A61M 1/342 604/5.01 |
| 2011/0082438 A1* | 4/2011 | Beck | A61M 5/142 604/500 |
| 2012/0083736 A1 | 4/2012 | Pfouts et al. | |
| 2012/0083737 A1 | 4/2012 | Beck | |

\* cited by examiner

INFUSION PUMP CASSETTE HAVING FINGER-BYPASSED IN-LINE OCCLUDER

FIELD OF THE INVENTION

The present invention relates generally to infusion pumps for controlled delivery of liquid food and medications to patients. More specifically, the present invention relates to a removable cassette by which an administration tubing set is operatively connected to an infusion pump, and a method of manually bypassing an in-line occluder of the cassette.

BACKGROUND OF THE INVENTION

Programmable infusion pumps are used to carry out controlled delivery of liquid food for enteral feeding and medications for various purposes, for example pain management. In a common arrangement, an infusion pump receives a disposable administration set comprising a cassette removably received by the pump and flexible tubing connected to the cassette for providing a fluid delivery path through the pump.

The administration set may include a pumping segment of tubing that wraps around a rotor mechanism of the pump, and the cassette may include a pair of tubing connectors to which opposite ends of the tubing segment are connected. The rotor mechanism may have pinch rollers or fingers that deform the tubing segment as the rotor rotates to progressively urge fluid through the tubing in a peristaltic manner. The cassette may have another pair of tubing connectors for connecting inflow tubing carrying fluid from a fluid source and outflow tubing leading to a patient. As a result, a flow path is provided from the inflow tubing, through the tubing segment, to the outflow tubing.

It is known to provide an in-line occluder as part of the cassette as a safety feature for preventing unintended free-flow of fluid to the patient if the pump is not in an operating mode. The in-line occluder may be incorporated into one of the tubing connectors of the cassette. A flow path passing the occluder may be intentionally established by engaging the flexible tubing at a predetermined location near the in-line occluder. For example, a projection on a door of the pump may be arranged to engage the tubing when the door is closed in order to open a flow path as disclosed in U.S. Pat. No. 7,815,612.

One challenge posed by in-line occluders is that they make it difficult for a person to manually prime the tubing of the administration set in order to remove air from the tubing and fill the tubing with liquid before infusion to a patient. While automated priming may be an option, wherein a user loads the administration set tubing into the pump and operates the pump to advance the fluid, automated priming has recognized drawbacks. For example, the pump may deliver fluid at a slow rate during priming and it can take quite a long time to complete priming. In emergencies, such a time delay may not be desirable. Another problem associated with using the pump for priming is that the attending person may begin to perform other tasks while automated priming continues, and may neglect to adequately monitor the administration set tubing as priming comes to completion. So, it is highly desirable to provide manual priming as an option.

The ENTERALITE® INFINITY® and INFINITY ORANGE® infusion pumps available from Zevex, Inc., the applicant herein, operate with a cassette having an in-line occluder. In order to manually prime the administration set, the user is instructed to gently pinch the tubing between the thumb and index finger at a location corresponding to the in-line occluder to open a flow passage, while also holding the bag of fluid above the cassette and squeezing the bag to force fluid past the occluder. If pinch pressure is too strong, or is applied in the wrong location, there is risk of damaging the in-line occluder and thereby hampering its effectiveness. There is also risk that the user will dig his or her fingernail into the tubing and puncture the tubing, thereby causing a leak.

In order to facilitate manual priming, it is known to provide a cantilevered priming arm on the cassette that extends alongside the tubing and has an actuator pad at the unsupported end of the arm. This type of priming arm is disclosed in U.S. Patent Application Pub. Nos. 2011/0082438 and 2012/0083737. The priming arm may be flexed to manually press the actuator pad against the tubing at a predetermined location to open a fluid passage past the occluder. The priming arm acts as a spring that removes the pad from the tubing when manual pressure is released so that the in-line occluder will once again block flow. This solution adds cost and complexity to the cassette design, and the flexible priming arm may break if the cassette is mishandled.

What is needed is a cassette that enables manual priming of the administration set tubing without the problems noted above.

SUMMARY OF THE INVENTION

A cassette for operatively connecting administration set tubing to an infusion pump has an in-line occluder for stopping flow, and is configured to enable a user to prime the administration set using a thumb and finger of one hand to manually create a flow passage in the tubing that bypasses the in-line occluder. In one embodiment, the cassette comprises a thumb tab that includes a thumb surface, and a tubing connector that includes an in-line occluder, wherein the in-line occluder is spaced laterally from the thumb tab. The cassette is configured such that a user's hand will cradle the cassette by pressing a thumb of the user's hand against the thumb surface and wrapping at least one finger of the user's hand around and under the thumb tab, whereby a user may apply pressure to tubing connected to the tubing connector at a location corresponding to the in-line occluder in a direction generally opposite to a direction in which the thumb is pressed against the thumb surface.

The invention is also embodied by a method of manually opening a flow passage in tubing connected to a cassette, wherein the cassette includes a tubing connector having an in-line occluder blocking flow through the tubing. The method generally comprises the steps of holding the cassette and tubing in a hand, pressing a thumb of the hand against a thumb surface on a thumb tab of the cassette, wrapping a finger of the hand around and under the thumb tab, and applying pressure with the finger to the tubing at a location corresponding to the in-line occluder in a direction generally opposite to a direction in which the thumb is pressed against the thumb surface.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
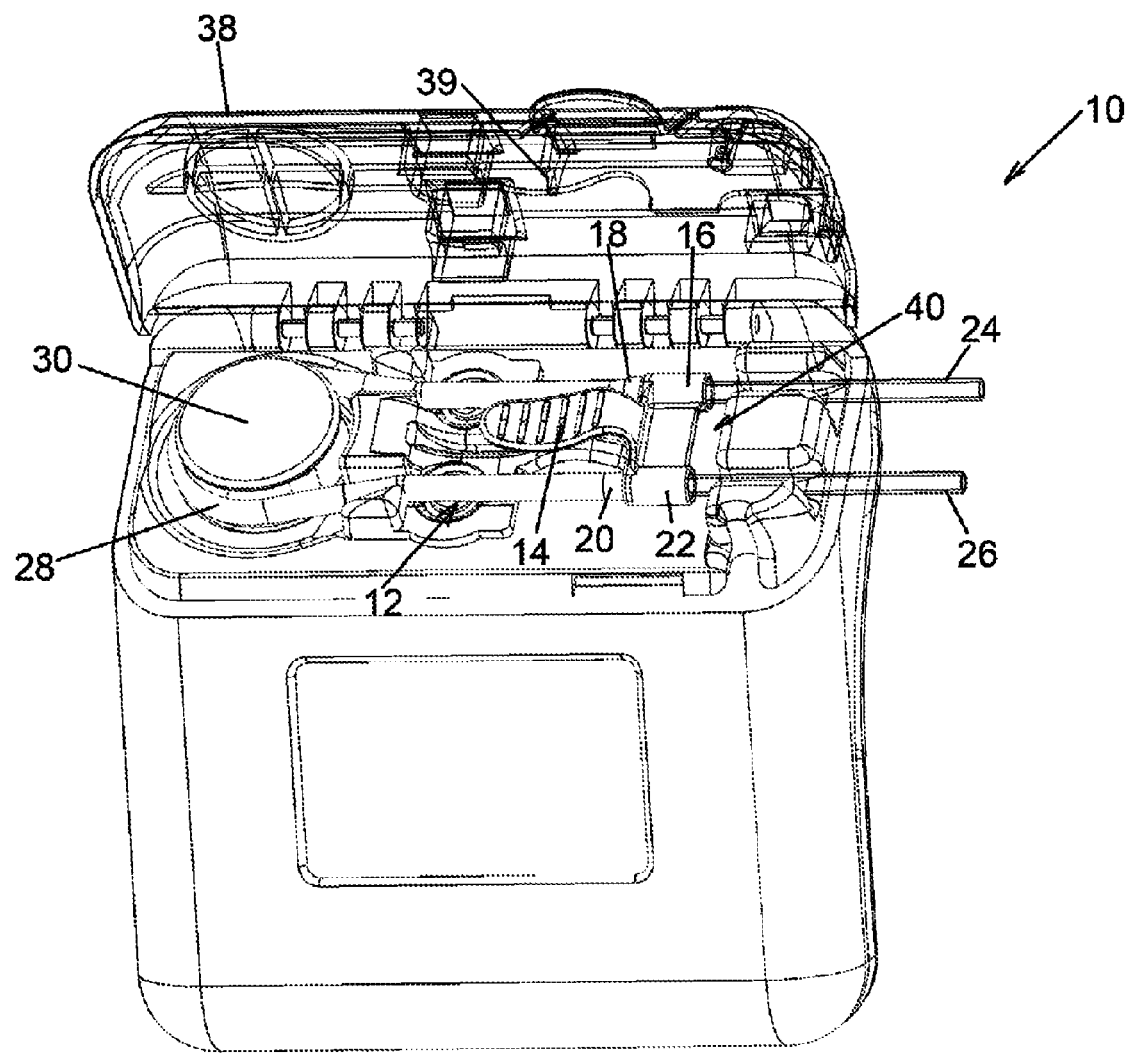
FIG. 1 is perspective view of an infusion pump, wherein an administration set having a cassette formed in accordance with an embodiment of the present invention is shown loaded in the infusion pump.
Figure 2:
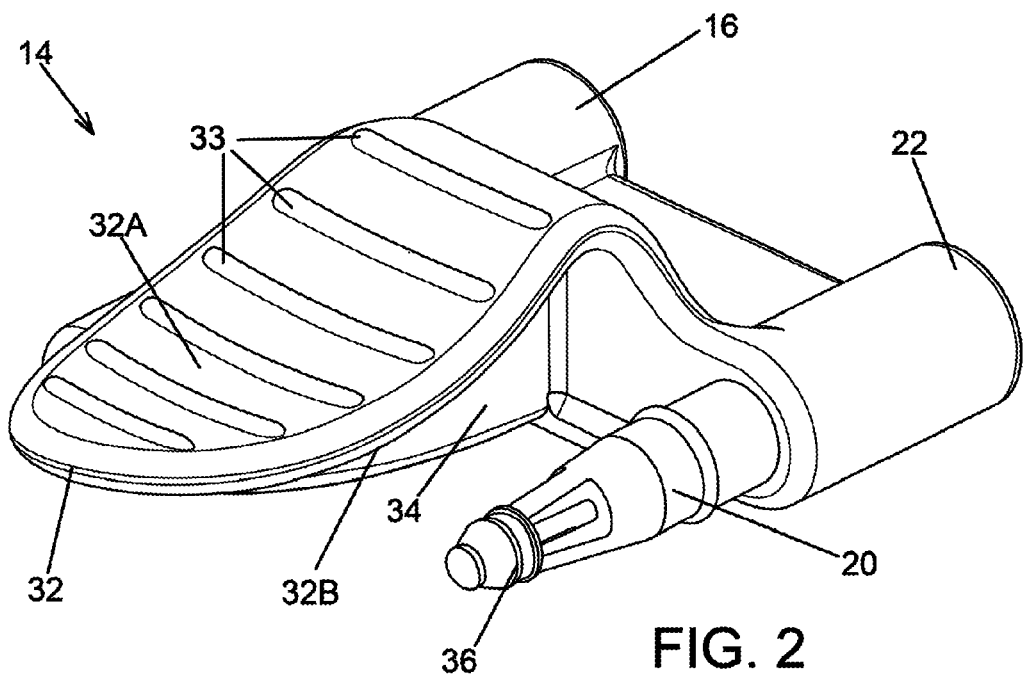
FIG. 2 is a perspective view of the cassette shown in FIG. 1, taken generally from above the cassette.
Figure 3:
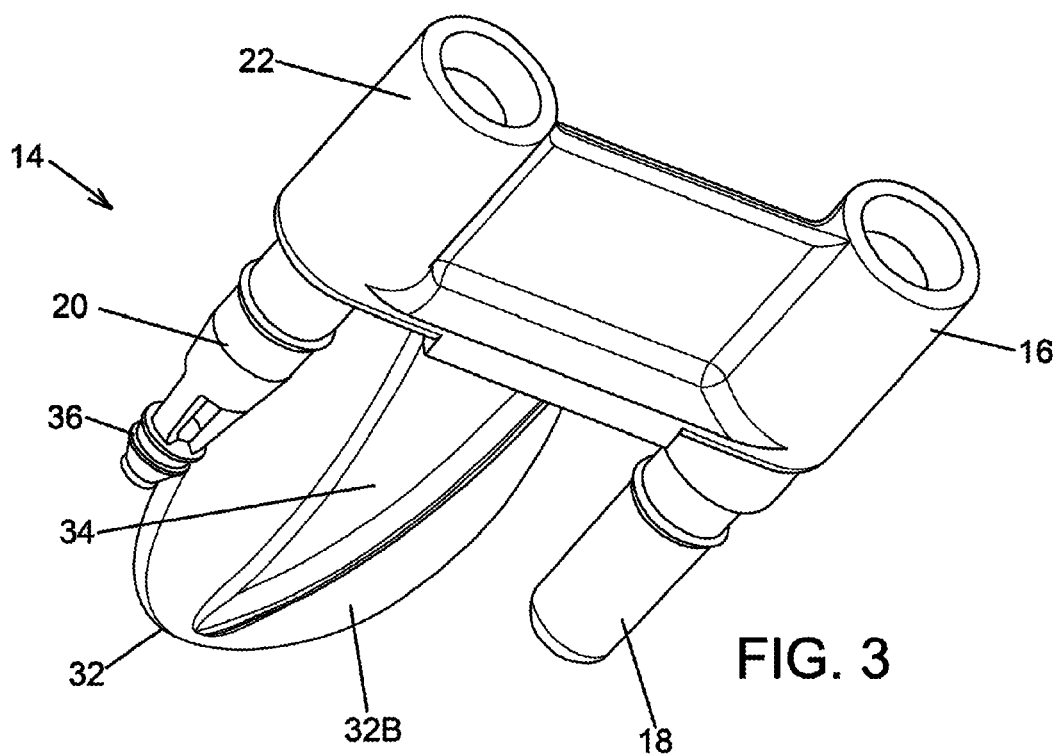
FIG. 3 is another perspective view of the cassette shown in FIG. 1, taken generally from below the cassette.
Figure 4:
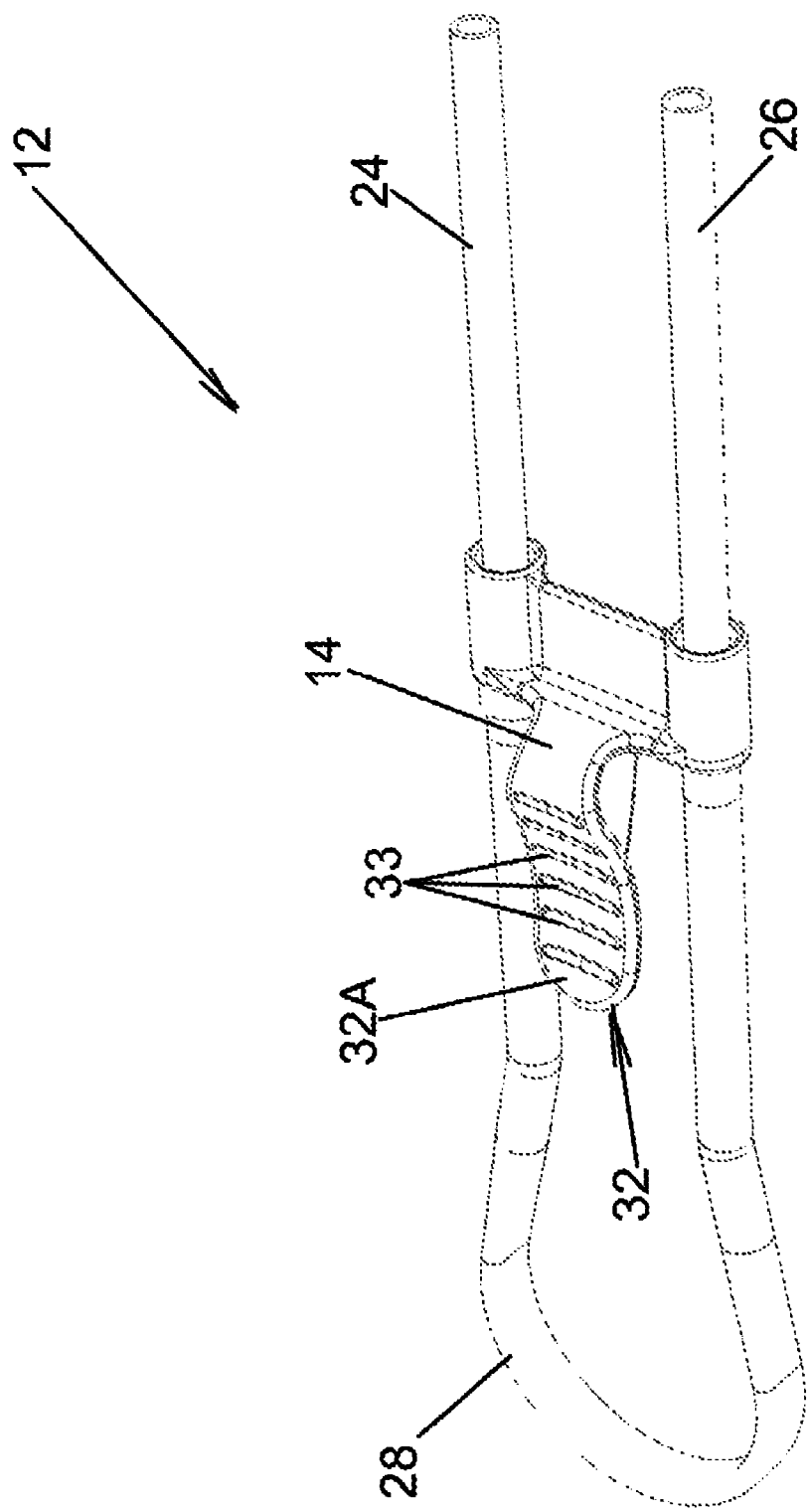
FIG. 4 is a perspective view of a pumping segment assembly of an administration set showing tubing of the administration set connected to the cassette.

FIG. 1 shows an infusion pump 10 in which an administration set 12 is removably received. Administration set 12 includes a cassette 14, which is shown by itself in FIGS. 2 and 3. Cassette 14 may include an inflow connector 16, an upstream pumping segment connector 18 in flow communication with inflow connector 16, a downstream pumping segment connector 20, and an outflow connector 22 in flow communication with downstream pumping segment connector 20. As shown in FIG. 4, administration set 12 may further include inflow tubing 24 having one end mated to inflow connector 16 and an opposite end (not shown) connected to a fluid source, and outflow tubing 26 having one end connected to outflow connector 22 and an opposite end (not shown) connected to a patient. Finally, administration set 14 may further include a pumping segment of tubing 28 having one end mated to upstream pumping segment connector 18 and an opposite end mated to downstream pumping segment connector 20.

In the illustrated embodiment, pump 10 is a rotary peristaltic pump having a rotor 30, wherein pumping segment 28 is wrapped around rotor 30 and is engaged by angularly spaced rollers on rotor 30 as the rotor rotates to provide peristaltic pumping action forcing liquid through the tubing of administration set 12. As may be understood by reference to FIG. 1, when rotor 30 rotates in a counter-clockwise direction, liquid is moved from inflow tubing 24 through inflow connector 16 and upstream pumping segment connector 18 to pumping segment 28, and then from pumping segment 28 through downstream pumping segment connector 20 and outflow connector 22 to outflow tubing 26. Although the present invention is described in the context of a rotary peristaltic pump, the invention is not limited to this type of infusion pump. The invention may be practiced with any type of infusion pump that receives an administration set having a cassette.

Cassette 14 includes an in-line occluder 36 which may be incorporated into downstream pumping segment connector 20. In-line occluder 36 prevents flow when pump door 38 is open. An actuator 39 on an underside of pump door 38 engages pumping segment 28 in a manner which opens a flow path around occluder 36 when door 38 is closed. As will be understood, preparing pump 10 for an infusion requires priming administration set 12 to remove air from the tubing. For this purpose, it is desirable that a user be able to manually open a flow passage past in-line occluder 36 when administration set 12 is outside of pump 10.

Figure 5A:
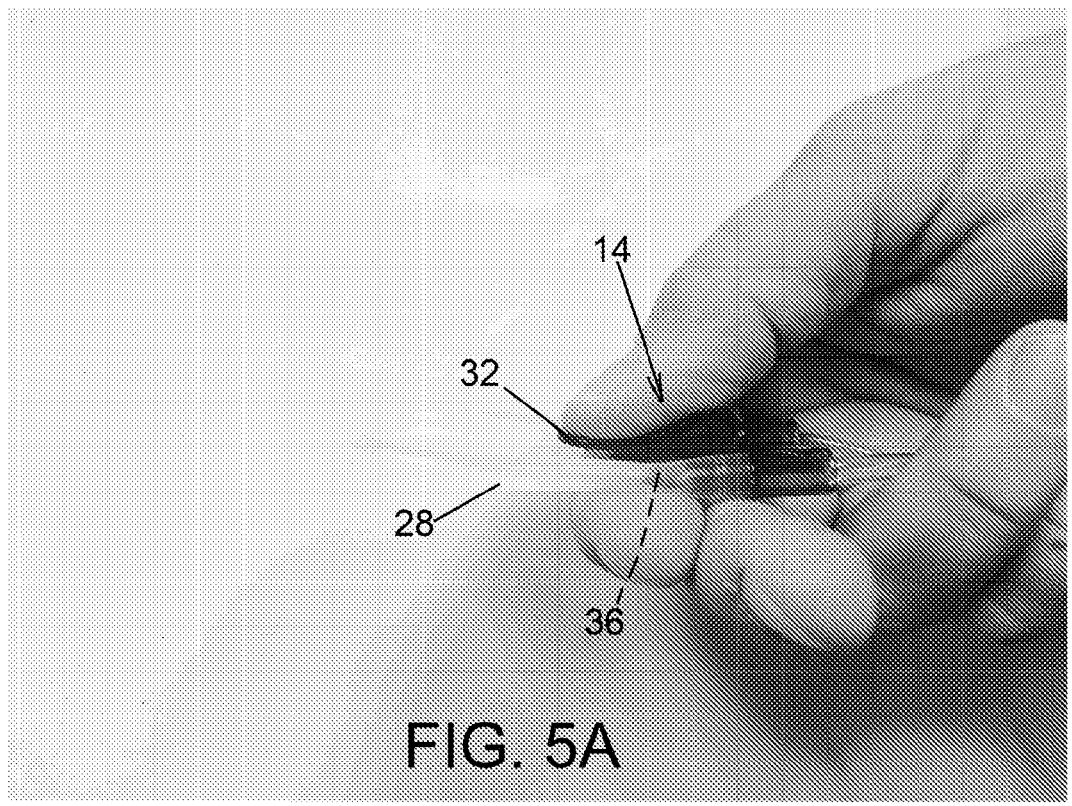
FIG. 5A is a perspective view showing a manual grip on the cassette and tubing in preparation for manual priming in accordance with an embodiment of the present invention.
Figure 5B:
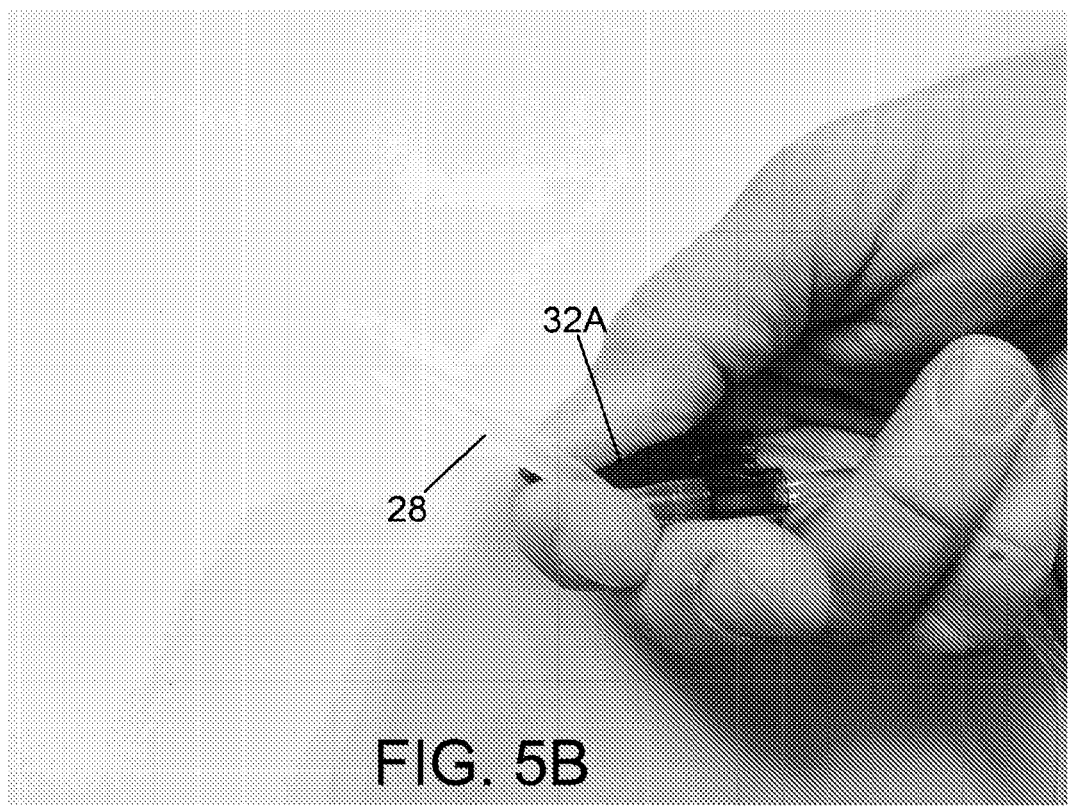
FIG. 5B is a view similar to that of FIG. 5A, however showing the application of manual pressure to the tubing in accordance with an embodiment of the present invention.

In accordance with an embodiment of the present invention, cassette 14 comprises a thumb tab 32 having an upwardly facing thumb surface 32A. As may be seen, in-line occluder 36 of downstream pumping segment connector 20 is spaced laterally from thumb tab 32. As a result, cassette 14 is configured for easy and intuitive manual bypass of in-line occluder 36 during priming. More specifically, FIGS. 5A and 5B illustrate that cassette 14 is configured such that a user's hand will cradle the cassette by pressing a thumb of the user's hand against thumb surface 32A and wrapping at least one finger of the user's hand around and under thumb tab 32. Thus, as shown in FIG. 5B, a user may apply pressure to tubing of pumping segment 28 connected to downstream pumping segment connector 20 at a location corresponding to in-line occluder 36. The applied pressure is in a direction generally opposite to a direction in which the thumb is pressed against thumb surface 32A, and will open a flow path past in-line occluder 36. In the embodiment shown, the index finger of the user's hand is used to apply pressure to pumping segment 28. Thumb surface 32A may be concave and may include traction ribs 33 to help prevent the user's thumb from slipping off thumb surface 32A.

The invention encompasses a method of manually opening a flow passage in tubing connected to a cassette including a tubing connector having an in-line occluder blocking flow through the tubing. The method comprises the steps of holding the cassette and tubing in a hand, pressing a thumb of the hand against a thumb surface on a thumb tab of the cassette, wrapping a finger of the hand around and under the thumb tab, and applying pressure with the finger to the tubing at a location corresponding to the in-line occluder in a direction generally opposite to a direction in which the thumb is pressed against the thumb surface.

The present eliminates the need for an additional component of the cassette, for example a flexing arm, to bypass activate the in-line occluder. The invention also eliminates the need to pinch two fingers onto the tubing, thereby avoiding risk of puncturing the tubing. This design utilizes the natural shape and fit in the users hand to bypass the in-line occluder in a more intuitive, cost effective, and reliable way.

While the invention has been described in connection with exemplary embodiments, the detailed description is not intended to limit the scope of the invention to the particular forms set forth. The invention is intended to cover such alternatives, modifications and equivalents of the described embodiment as may be included within the scope of the invention.

What is claimed is:

1. A cassette for operatively connecting administration set tubing to an infusion pump, the cassette comprising:
 a thumb tab including a thumb surface; and
 a tubing connector elongated in a longitudinal direction, the tubing connector including an in-line occluder, wherein the in-line occluder is spaced laterally but not longitudinally from the thumb tab;
 wherein the thumb tab is not a flexing arm deflectable against the tubing to bypass the in-line occluder
 wherein the cassette is configured such that a user's hand will cradle the cassette by pressing a thumb of the user's hand against the thumb surface and wrapping at least one finger of the user's hand around and directly under the thumb tab, whereby a user may apply pressure to tubing connected to the tubing connector at a location corresponding to the in-line occluder in a direction orthogonal to the longitudinal direction of the tubing connector and generally opposite to a direction in which the thumb is pressed against the thumb surface to open a flow passage past the in-line occluder.

2. The cassette according to claim 1, wherein the thumb surface is concave.

3. The cassette according to claim 1, wherein the thumb surface includes traction ribs.

4. A method of manually opening a flow passage in tubing connected to a cassette, the cassette including a tubing connector elongated in a longitudinal direction, the tubing connector having an in-line occluder blocking flow through the tubing, the method comprising the steps of:
   holding the cassette and tubing in a hand;
   pressing a thumb of the hand against a thumb surface on a thumb tab of the cassette;
   wrapping a finger of the hand around and directly under the thumb tab, wherein the thumb tab is not a flexing arm deflectable against the tubing to bypass the in-line occluder; and
   applying pressure with the finger to the tubing at a location corresponding to the in-line occluder in a direction orthogonal to the longitudinal direction of the tubing connector and generally opposite to a direction in which the thumb is pressed against the thumb surface.

5. The method according to claim 4, wherein the finger is the index finger of the user's hand.

\* \* \* \* \*